United States Patent [19]
Adamo

[11] Patent Number: 5,343,561
[45] Date of Patent: Sep. 6, 1994

[54] SLEEPING MASK AND NECK REST

[76] Inventor: Renè Adamo, Drei-Eichen-Weg 41, Salzburg, Austria

[21] Appl. No.: 671,772
[22] PCT Filed: Feb. 15, 1990
[86] PCT No.: PCT/EP90/00247
§ 371 Date: Jun. 14, 1991
§ 102(e) Date: Jun. 14, 1991
[87] PCT Pub. No.: WO91/02502
PCT Pub. Date: Mar. 7, 1991

[30] Foreign Application Priority Data

Aug. 17, 1989 [AT] Austria ............... 1952/89

[51] Int. Cl.$^5$ ............................................. A61F 9/04
[52] U.S. Cl. ............................................. 2/15; 2/174; 2/206
[58] Field of Search ............... 2/15, 206, 9, 173, 207, 2/423, 11, 174

[56] References Cited

U.S. PATENT DOCUMENTS

| | | | |
|---|---|---|---|
| 849,548 | 4/1907 | Lineweaver | 2/206 |
| 945,839 | 1/1910 | Brisbane | 2/206 X |
| 960,520 | 6/1910 | Dysthe | 2/206 |
| 1,035,217 | 8/1912 | McQuary, Jr. | 2/206 X |
| 1,047,163 | 12/1912 | Bullock | 2/15 |
| 1,923,340 | 8/1933 | Steckler | 2/174 |
| 1,924,315 | 8/1933 | Hemphill et al. | 2/15 |
| 2,537,768 | 1/1951 | LaPorte | 2/15 |
| 2,763,869 | 9/1956 | Bogart et al. | 2/174 |

OTHER PUBLICATIONS

PCT Application No: WP 86/00012; Jan. 3, 1986 International Publication.

Primary Examiner—Peter Nerbun
Attorney, Agent, or Firm—Fliesler, Dubb, Meyer & Lovejoy

[57] ABSTRACT

For an improved fastening of a sleeping mask (1) to the head and for providing a certain noise protection, a holding device is formed by side parts (4,4') which are extended into a region adjacent to a wearer's ears and pertain to eye mask (2) and comprise receiving pockets (7,7') for the outer ears on the inner side facing the head. A drawstring has one end secured to the eye mask and a free end projecting out of a recess in a lower edge of the eye mask. The drawstring is pulled to secure the outer rend of the wearer in a receiving pocket.

13 Claims, 4 Drawing Sheets

SLEEPING MASK AND NECK REST

This invention relates to a sleeping mask.

A sleeping mask is known from U.S. Pat. No. 2,243,982. In the embodiment illustrated in FIGS. 1 and 2 of U.S. Pat. No. 2,243,982, a curved slit is provided in each side part of the eye mask, resulting in a C-shaped opening with a bow into which the outer ear of a user may be inserted, whereby the known sleeping mask is secured to the user's head. Furthermore, the curved slit creates a strip or tongue which covers the ear opening when the mask is worn. Said tongue can also be crumpled and inserted into the ear as a kind of plug.

First of all, the sleeping mask of the generic type is disadvantageous insofar as the bow which is formed by an incision tears relatively easily, as there is only a small strap which is very easily damaged, especially when slipped over the ear. Moreover, the ear cover and thus the sound absorption are not very satisfactory. Although sound absorption can somewhat be improved by crumpling the tongue formed, this, in turn, has the disadvantage that the plug inserted into the ear presses on the ear during a long period of use and becomes thus uncomfortable for the user.

U.S. Pat. No. 2,942,270 discloses another sleeping mask in the case of which the eye mask is secured to the ears with the aid of two cord-like fastening strings. The free ends of the fastening strings comprise earplugs which are inserted into the ears for the purpose of sound absorption. The main disadvantage of this known sleeping mask is the relatively low degree of wearing comfort, as the fastening strings which are guided around the ears may cut into the user's skin. Moreover, with this type of sleeping mask, the plugs inserted into the ears will become uncomfortable over a long period of use.

Other sleeping masks that are known from U.S. Pat. No. 2,342,840, DE-U-8 808 220 and DE-A-3 920 954 are provided with fastening means, e.g. in the form of an elastic which is guided around the back of the user's head. A considerable disadvantage is here that the fastening means guided around the back of the head is not only considered to be troublesome, but is also retained by the headrest during movement of the head, so that the eye mask will slip out of place time and again. Furthermore, the sleeping mask known from U.S. Pat. No. 2,342,840 does not provide any noise protection, and the two other last-mentioned sleeping masks of the prior art have the added disadvantage of being costly to manufacture due to their extravagant construction.

It is therefore the object of the present invention to provide a sleeping mask of the type specified in the preamble of claim 1, which sleeping mask is of a simple construction and allows a good and comfortable fit of the eye mask without the danger of the eye mask slipping out of place during head movement on a headrest.

With a sleeping mask of the generic type comprising an eye mask as well as a holding device for securing the mask to the head of a user, this object is attained in that the fastening means which are mounted on both side parts of the eye mask are formed as receiving pockets.

Since the side parts of the eye mask extend up to the ears and comprise pockets for receiving the outer ears, there is no longer any need for the eye mask to be closed via a holding device reaching round the back of the head because the eye mask can now be secured via the extended side parts to the outer ears engaging the respective receiving pockets. The back of the head which is free of any holding device for holding the eye mask can thus be moved on a headrest without slippage of the eye mask having to be feared. Furthermore, the pockets which serve to receive the outer ears will hardly interfere with a hairstyle which, in turn, cannot be ruined by the receiving pockets as is the case with elastics encircling the back of the head.

The receiving pockets which are provided on the inner side facing the head and serve to receive the outer ears are not only securely held within the sleeping mask of the invention, but also offer an excellent cover for the outer ears, resulting in sound proofing that turns out to be advantageous, especially with background noise, such as street noise, ventilation sounds of air conditioners, or the like. The sound absorbing effect of the receiving pockets used for receiving the outer ears can be considerably increased by providing the extended side parts in the ear region with a sound absorbing material.

For an optimum adaptation to anatomical conditions, the sleeping mask of the invention is preferably provided with a curved outer edge extending in wavelike fashion. As a result, the side parts and their receiving pockets used for entirely covering the outer ears have a substantially round or oval shape and are connected via narrowed transition portions, which are of a reduced size in comparison with the side parts, to eye covering portions of a likewise enlarged size. The eye covering portions, in turn, are interconnected via a nose portion which is also narrowed and thus of a reduced size and which may preferably be provided with contact pads that rest on the outer sides of the nose when the mask is worn, and thereby further increase the wearing comfort and the secure fit. Likewise, the inner surfaces of the receiving pockets may be provided with sound absorbing inserts which, when the mask is worn, rest on the opening of the outer ear and thereby improve the sound absorption considerably. Finally, the eye portions may also be provided with contact pads which considerably improve the wearing comfort on the one hand and the dimming effect on the other hand.

The subclaims relate to advantageous developments of the invention.

If the receiving pockets are formed by the respective inner surfaces of the side parts and by a planar holding member consisting e.g. of a flexible fabric, this has the advantage that the inner surface of the eye mask can be integrally extended into the side portions or, in other words, the inner surface of the eye mask and that of the side portions may be one part. Only the holding member, which preferably consists of a fabric, such as silk or the like, will then be sewn onto the ear portion of the side parts, resulting in an insertion opening into which the outer ear is inserted for fixing the sleeping mask of the invention. The inner surface and the holding member that form the respective receiving pocket of the side parts will then surround the ear entirely, so that the latter is entirely covered on the one hand and the sleeping mask is simultaneously secured to the user's head on the other hand.

For an improved fit, the opening edge of the respective receiving pocket may either be stiffened or provided with a drawstring which makes it possible to pull the opening edge together and thereby fix the sleeping mask.

To secure the fixing position, the free end of the drawstring may be provided with a fixing button which may e.g. be formed as a press stud comprising a springloaded actuation member which in the fixing position clamps and thus secures the respective portion of the free end of the drawstring.

For instance, to be able to adjust a standard size to different head sizes, the transition portion between the eye mask and the side parts may be made elastically stretchable. To this end, it is possible to design the transition portion as an elastic band which is inserted between the eye mask and the side part. This has the advantage that despite varying head sizes the eye mask can always be the same as far as its dimensions and the position of the possibly provided contact pads are concerned, as an adaptation to different head sizes is possible via the elastic transition portion which, however, when stretched or drawn together, does not affect the position of the eye mask relative to the head.

Furthermore, the sleeping mask of the invention can be adapted to the respective anatomical requirements in a simple way by constructing the side parts of the eye mask such that their length is variable. This can be achieved with rubber bands, with Velcro-type connections, clasps or the like.

Furthermore, the extension of the eye mask into side parts forming a holding device ensures the possibility of a broad-surfaced fit of the sleeping mask in the region of the temples and has the advantage that the eye mask does not wrinkle in the area of the outer corner of the eye, which would greatly impair the fit of the eye mask. If the side parts have a minimum width adapted to the average distance between the upper part of the eyebrow and the lower edge of the eye, this danger can be substantially eliminated, even if there is excessive pull, especially when the eye mask is provided in the eye and nose portions with corresponding contact pads. It should here be noted that, for medical reasons, contact with the cornea should be avoided as much as possible when the eye is open. This can preferably be accomplished with the aid of said contact pads which rest on the eyelids when the mask is worn and can largely prevent the eyes from opening.

The present invention also relates to a neck rest of the type specified in the preamble of claim 10. Such a neck rest is e.g. known from DE-A-3 430 725. Another neck rest is known from DE-U-8 622 024. However, none of these known neck rests is satisfactory due to their construction, in particular that of their side legs, as practical experience has shown that despite many efforts they cannot prevent the user's head from tilting and their design is thus in need of improvement.

Therefore, it is also the object of the present invention to provide a neck rest of the type specified in the preamble of claim 10, which neck rest prevents the user's head from tilting, in particular during sleep in a sitting position.

With the neck rest specified in the preamble of claim 10, which has a waist and two side legs extending in mirror-symmetrical fashion relative to the cross-sectional area of the waist, this object is attained in that the side legs become gradually thicker from the waist towards their front end portions so as to have at these ends a cross-sectional dimension which is at least 1.5 times that of the waist.

This results in a collar-shaped neck rest or neck roll which is substantially U-shaped when viewed from above and which nestles against the nape of the neck and the lower cheekbones when being used. A safe support of the user's head is here obtained due to the balloon-shaped and considerably thickened end portions.

Subclaims 11 and 12 relate to advantageous developments of the neck rest of the invention.

An especially preferred size of the end portions is two times the cross-sectional dimension of the waist, with a preferably circular cross-section being chosen for the end portions to obtain said balloon-like configuration.

A configuration which gradually tapers from the thickened end portions towards the waist is created thereby, and also by the construction according to claim 10. Such a configuration offers an especially high degree of wearing comfort as well as a safe support.

In order to prevent the neck rest from slipping, the end portions may be interconnected, preferably by means of a cord of an adjustable length.

The neck rest is preferably of an inflatable type and, to this end, may be made from an airtight material, preferably from plastics. To increase the wearing comfort, said inflatable material may be coated with a soft material which is preferably washable.

Furthermore, it is possible to construct the neck rest of the invention in three basic sizes, e.g. for adults, adolescents and children.

Other details, features and advantages of the invention will become apparent from the following description of embodiments taken in connection with the drawing, wherein FIG. 1 is a top view of the inner surface of a first embodiment of a sleeping mask of the invention;

Figures 1, 2:
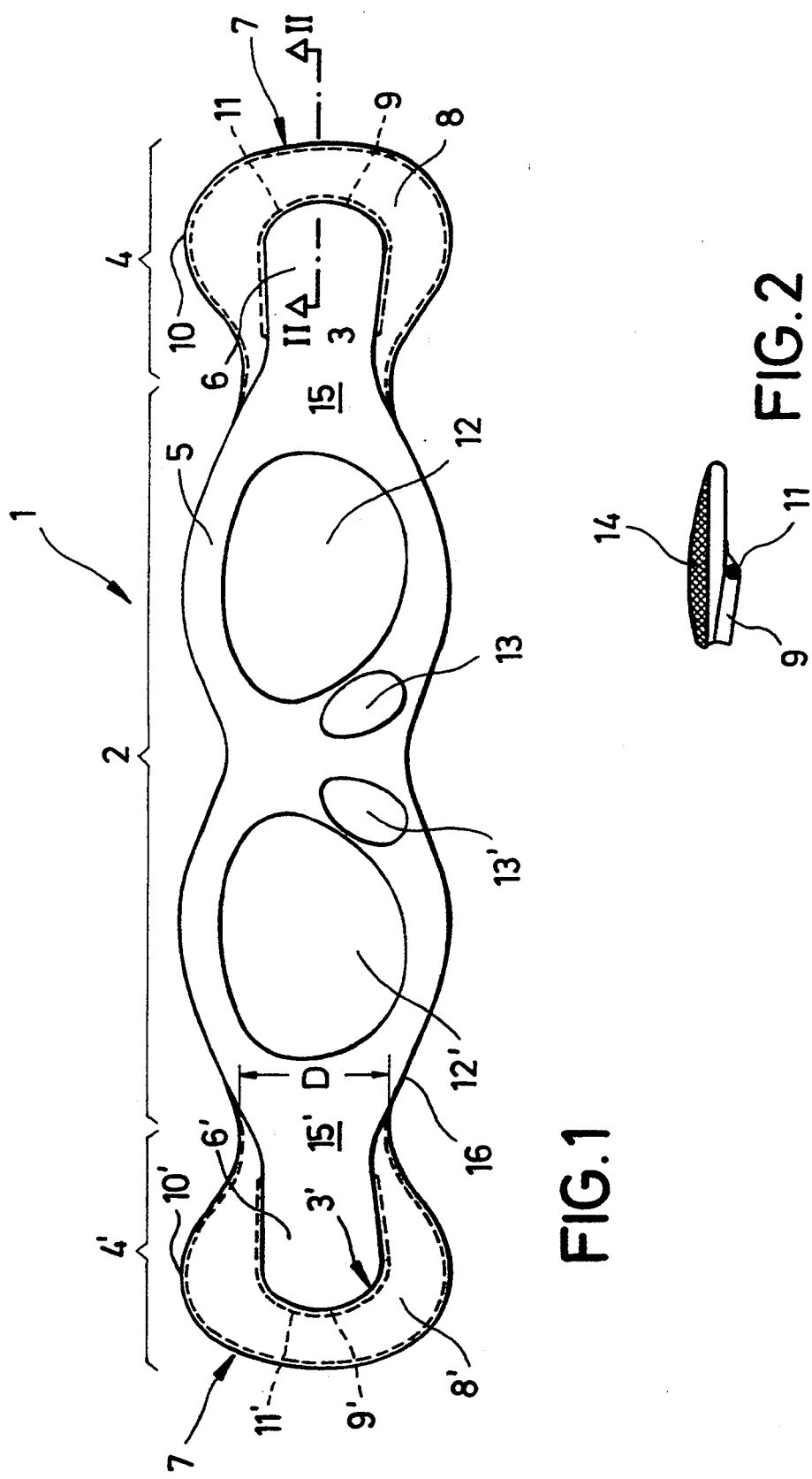
FIG. 2 is a sectional view taken along line II—II in FIG. 1.

FIG. 1 depicts a first embodiment of a sleeping mask 1 of the invention. Sleeping mask 1 comprises an eye mask the whole of which is designated by reference numeral 2, as well as a two-part holding device 3,3' for securing eye mask 2 to the head of a user.

Eye mask 2 is provided with two side parts 4,4' which in the embodiment are integrally connected to eye mask 2. Side parts 4,4' join said eye mask 2 at the opposite ends thereof.

Eye mask 2 comprises an outer surface, which cannot be seen in FIG. 1, and an inner surface 5 which faces the user's eyes when sleeping mask 1 is worn. As a result of the integral design in the embodiment illustrated in FIG. 1, the inner surface 5 is continued by the inner surfaces 6 and 6' of side parts 4 and 4', respectively. Likewise, the outer surface of eye mask 2 (which surface cannot be seen in FIG. 1) is continued by the outer surfaces of side parts 4,4' (which surfaces are also not visible).

Furthermore, each of side parts 4, 4' comprises a fastening means for securing eye mask 2 to the outer ears of a user. These means are formed as receiving pockets 7 and 7'. As becomes apparent from FIG. 1, receiving pockets 7, 7' are each formed by the inner surface 6 and 6', respectively, of side parts 4, 4' and by a holding member 8 and 8', respectively. As becomes also apparent from FIG. 1, holding members 8, 8' are formed in the embodiment as substantially C-shaped strips which are preferably made of a fabric, such as silk or the like. Holding members 8,8' comprise a free unattached opening edge 9 and 9', respectively, and an outer edge 10, 10' which is firmly connected, preferably sewn, to side parts 4 and 4', respectively. The broken line drawn in FIG. 1 in the area of the outer edges 10, 10' represents the seam running along the entire outer edge 10 and fixing the cloth-like holding member 8 and 8', respectively, to the inner surface 6 and 6', respectively, of side parts 4,4'. This creates the bag-like receiving pockets 7,7' which are dimensioned such that the outer ear of a user can be enclosed by them more or less completely.

In the embodiment illustrated in FIG. 1, the opening edges 9,9' are stiffened. To this end, edges 9,9' may comprise sewn-in stiffenings 11 and 11', respectively, which consist e.g. of whalebone.

For a better adaptation of eye mask 2 or sleeping mask 1 to anatomical conditions, eye mask 2 may be provided in the eye and nose regions with contact pads 12, 12' for the eyes and contact pads 13, 13' for contact with the lateral nose surfaces.

For a good sound absorption, side parts 4,4' may additionally be provided in the ear portion, i.e. in the region of receiving pockets 7, 7' with an insert of a sound absorbing material 14, as becomes apparent from the sectional view of FIG. 2.

The length of sleeping mask 1 can be adapted to the ear distance, which is measured along the eye mask, by means of a corresponding length adjustment of side parts 4,4. For this purpose, side parts 4,4' may be equipped with pleats that are possibly subjected to an elastic tensile stress.

Furthermore, it is possible to make the transition portions 15 and 15' between eye mask 2 and side parts 4, 4' elastically stretchable. To this end, transition portions 15, 15' may be formed as an elastic band which is sewn in place between the end portions of eye mask 2 and the adjoining portions of side parts 4 and 4'.

The width of side parts 4,4' should be adapted in the ear portion to the ear size, but not in the transition portion 15, 15' towards eye mask 2. To reliably prevent eye mask 2 from wrinkling in the region of the outer corner of the eye, it is recommended that the minimum width D of side parts 4,4' be adapted to the average distance between the upper line of a person's eyebrow and the lower edge of the eye, whereby a sufficiently large planar contact area is obtained in the region of the temples.

As becomes also apparent from FIG. 1, the outer edge 16 which encircles the entire sleeping mask 1 extends in a wavelike manner. This results in enlarged dimensions in the regions of side parts 4, 4' and of the inner surface portions of eye mask 2 which comprise contact pads 12, 12' for the eyes. The wavelike course of edge 16 results from the dimensions B,C,D, and E shown in FIG. 4, which are specified in the following Table for men and women:

|   | Men's Sizes | Women's Sizes |
|---|---|---|
| A | 20.5 | 19.0 |
| B | 3.5 | 3.5 |
| C | 8.5 | 8.5 |
| D | 5.5 | 5.5 |

-continued

|   | Men's Sizes | Women's Sizes |
|---|---|---|
| E | 9.0 | 9.0 |
| F | 14.0 | 13.5 |
| G | 13.5 | 13.0 |

Figure 3:
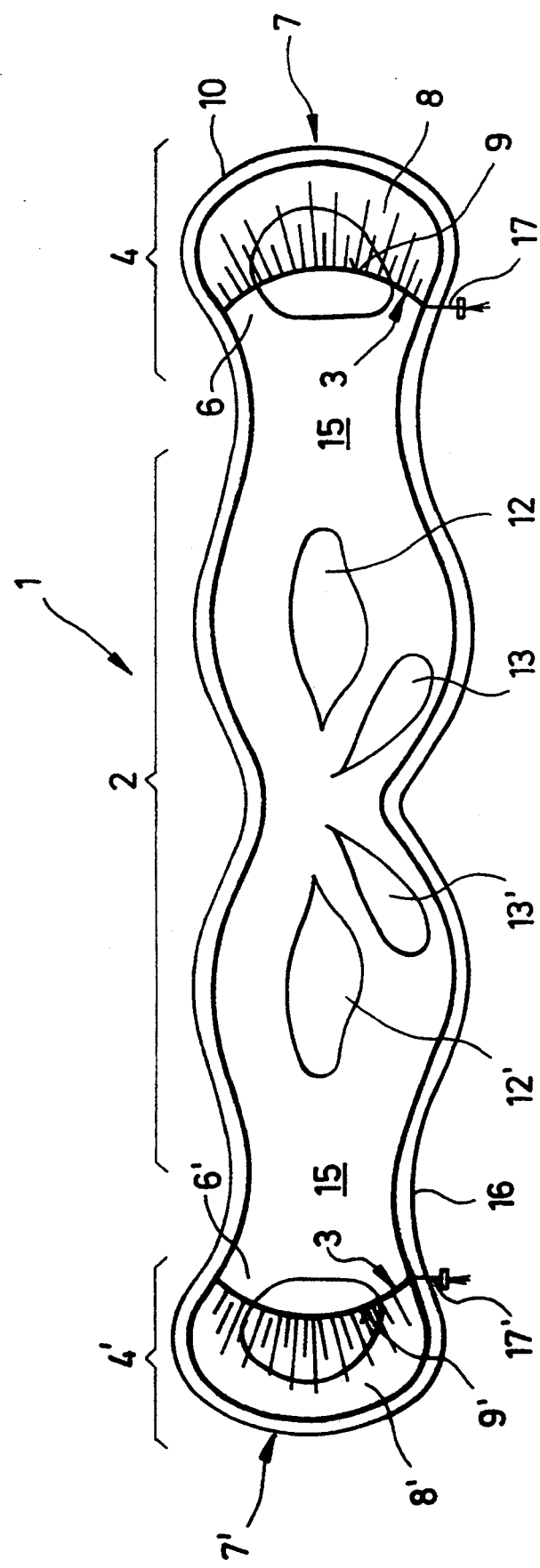
FIG. 3 is an illustration of a second embodiment of the sleeping mask of the invention in accordance with FIG. 1.
Figure 4:
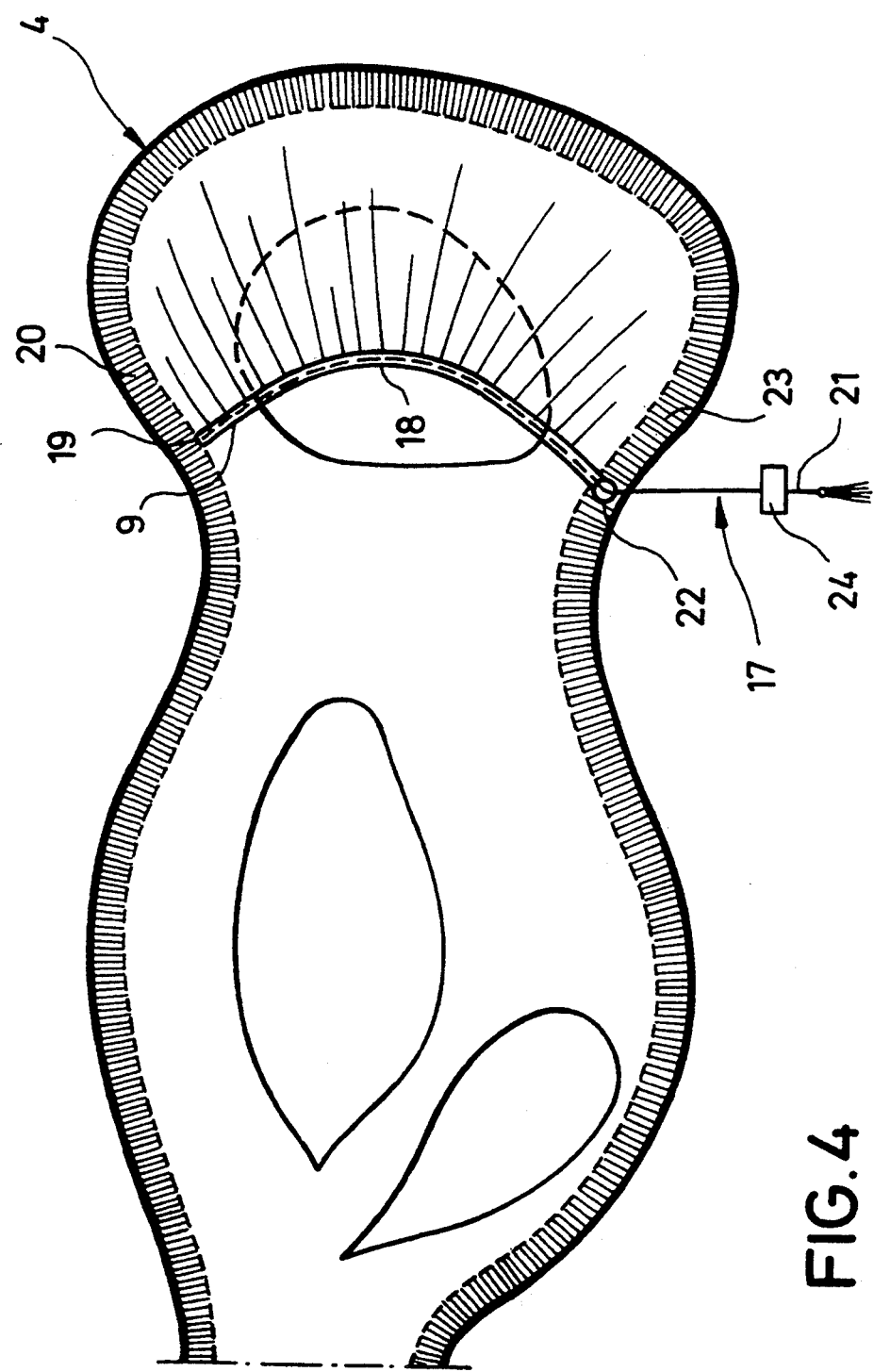
FIG. 4 is an enlarged view of the right part of the sleeping mask in accordance with FIG. 3.

The dimensions listed in this Table are all given in cm and may pertain to the embodiment illustrated in FIGS. 4 and 3 and the embodiment shown in FIGS. 1 and 2. Furthermore, these dimensions are only an example of common sizes for Central Europeans. All kinds of adjustments are here possible.

Furthermore, FIGS. 1, 3 and 4 show that the dimensionally reduced portions between side parts 4,4' and eye mask 2 and between eye contact portions 12,12' and nose contact portion 13, 13' are rounded, resulting in the already mentioned wavelike shape. This wavelike shape offers a particulary high degree of wearing comfort and is very well adapted to anatomical requirements.

The embodiment illustrated in FIGS. 3 and 4 corresponds largely to that shown in FIGS. 1 and 2. Hence, the same reference numerals as in FIGS. 1 and 2 are used for designating identical parts.

One of the main differences between the two embodiments is that holding member 8, 8' has a broader surface area and thus rather takes on the form of a strip with rounded-off longitudinal edges, as can be seen in detail in the illustration of FIG. 3.

Furthermore, opening edges 9 and 9' of receiving pockets 7 and 7' are each provided with a drawstring 17 and 17', respectively. This shall be described in the following with reference to FIG. 4. Reference is here only made to drawstring 17 because this member is constructed in the same way as drawstring 17'. As illustrated in FIG. 4, drawstring 17 extends along opening edge 9 and is arranged in a reception channel defined by a seam 18 which extends along opening edge 9. The seam 18 forms a reception channel for drawstring 17. One end 19 of drawstring 17 is here secured to the upper edge 20 of side part 4, while the free end 21 is guided out of a recess 22 provided in the lower edge 23 of side part 4. The free end 21 is provided with a fixing button 24 which can fix the respective fixing position of drawstring 17.

The embodiments illustrated in FIGS. 1–4 and regarding sleeping mask 1 of the invention may be of different qualities. It is e.g. possible to provide a more or less "one-way" or disposable version using substantially cheap materials, so that sleeping mask 1 can be thrown away after one use.

However, it is also possible to construct sleeping mask 1 as a completely washable type which can be used several times. Preferred materials are here above all leather for the eye mask and the side parts, and a textile, in particular silk, for the holding members.

If sleeping mask 1 is to be used, it is put on the eyes and nose area together with eye mask 2 and then secured to the outer ears, the latter being inserted into receiving pockets 7,7' through the insertion openings defined by opening edges 9,9'. Either the stiffened opening edge or the pulled drawstring 17, 17' securely holds the outer ear in receiving pocket 7,7'.

Figure 5:
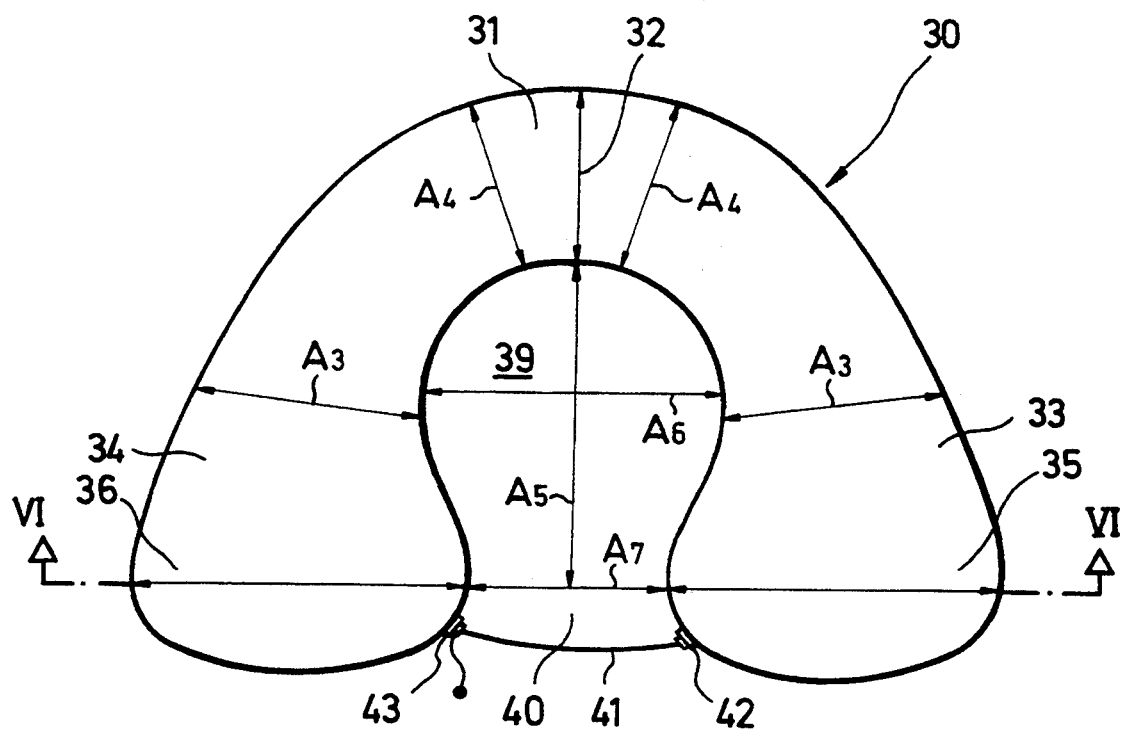
FIG. 5 is a top view of a neck rest of the invention.
Figure 6:
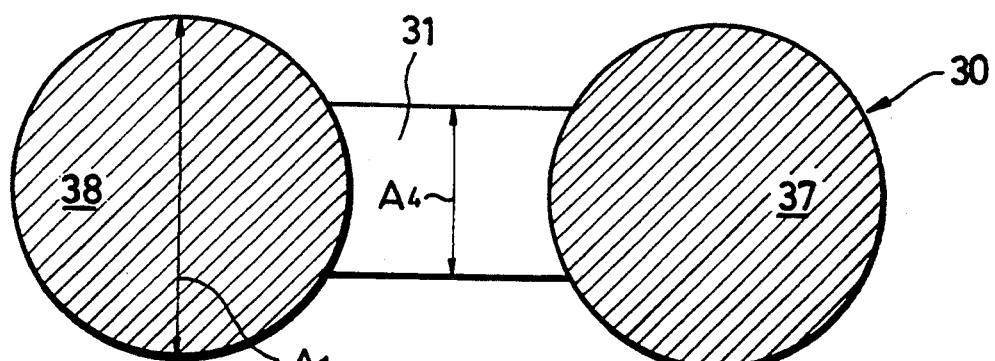
FIG. 6 is a partly sectioned front view of the neck rest in accordance with FIG. 5 from the direction of arrows VI—VI.
Figure 7:
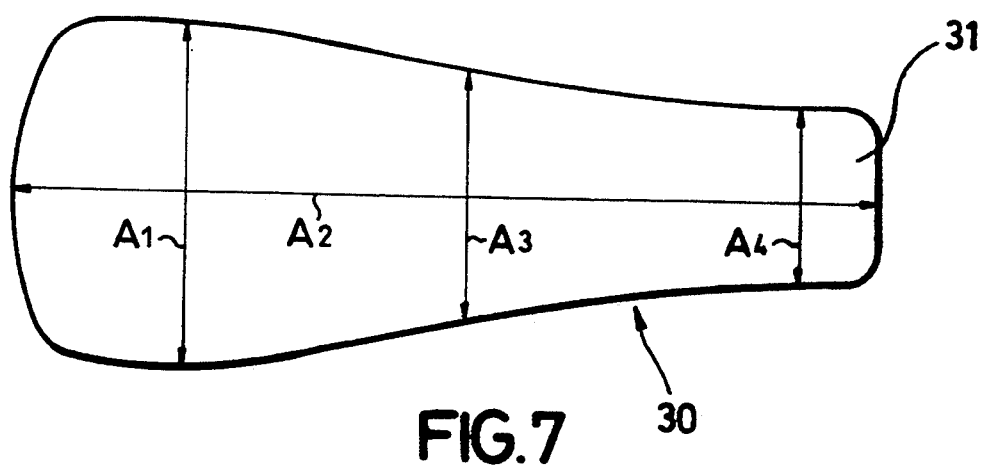
FIG. 7 is a side view of the neck rest in accordance with FIGS. 5 and 6.

FIGS. 5–7 illustrate a preferably inflatable neck rest 30 of the invention which comprises a waist 31 and two side legs 33 and 34 extending in mirror-symmetrical fashion relative to the cross-sectional waist area 32 in the same direction. As shown in FIG. 5, a substantially U- or V-shaped configuration follows from such a construction. Side legs 33 and 34 comprise front end portions 35 and 36 whose cross-sectional areas 37 and 38, respectively, illustrated in FIG. 6, are preferably circular. Furthermore, the size of end portions 35 and 36, or their cross-sectional area 37, 38, is at least 1.5 times larger than the cross-sectional dimension of waist 31. In the embodiment illustrated in FIGS. 5-7, the cross-sectional size is preferably two times that of waist 31. As can especially be seen in FIG. 7, this results in side legs 33, 34 which become gradually thicker from waist 31 onwards. This creates a substantially circular neck receiving portion 39 having a dimensionally narrowed insertion portion 40, as becomes especially apparent from the top view of FIG. 5.

As is also shown in FIG. 5, end portions 35 and 36 are interconnected via a cord 41 which is preferably adjustable in length and held via fastening members 42 and 43. Fastening member 43 has a preferably self-locking throughhole for fixing cord 41 in the respectively adjusted state.

An especially preferred embodiment of neck rest 30 illustrated in FIGS. 5 to 7 (which embodiment provides, however, only one possible example) has the dimensions A1–A7 shown in said FIGURES, with the dimensions being listed in the following Table:

$$A1=14\ A2=23.5\ A3=10\ A4=7\ A5=13\ A6=13$$
$$A7=8.$$

All dimensions are given in cm.

Neck rest 30 of the invention has the advantage that the head of a user whose neck is disposed in receiving portion 39 is fixed, especially when this person sleeps in a sitting position. This ensures a high degree of wearing comfort and a sound sleep.

Furthermore, sleeping mask 1 depicted in FIGS. 1–4 and neck rest 30 may preferably be used in combination. This provides a sleeping aid system which has turned out to be especially advantageous, in particular for long-distance travellers during long-distance flights, in cars, on ships or on trains. With these types of travel, even the use of sleeping mask 1 or neck rest 30 alone offers considerable advantages in comparison with conventional sleeping masks and neck rests.

I claim:

1. In a sleeping mask adapted to be mounted to a users had in covering light blocking relation over the users eyes, the sleeping mask having an eye mask having an outer surface, an inner surface, and opposite ends, the inner surface being adapted to face the user's eyes, and a holding device for securing said eye mask to the head of the user, the improvement wherein:

the holding device comprises two side parts of the eye mask which join the opposite ends of said eye mask and which comprise outer and inner surfaces in extension of said outer and inner surfaces of said eye mask and of which each comprises a receiving pocket for securing said eye mask to the outer ears of the user, each of said receiving pockets being formed by said inner surface of said side parts and by a holding member having a free opening edge and an outer edge connected firmly to said side part, said opening edge being provided with a drawstring which is passed through a seam extending along said opening edge, the drawstring having a secured end secured to an upper edge of said side part and a free end which projects out of a recess provided in a lower edge of said side part.

2. A sleeping mask as defined in claim 1, characterized in that said opening edge is stiffened.

3. A sleeping mask as defined in claim 1, characterized in that said free end is provided with a fastening button.

4. A sleeping mask as defined in claim 3, characterized in that the length of said side parts is variable.

5. A sleeping mask as defined in claim 4, characterized in that a pair of transition portions are provided, each transition portion extending between said eye mask and one of said side parts, the transition portions being elastically stretchable.

6. A sleeping mask as defined in claim 5, characterized in that said transition portions have a minimum width adapted to an average distance between an upper line of an eyebrow and a lower edge of an eye of the user's head.

7. A sleeping mask as defined in claim 6, characterized in that said eye mask comprises two eye portions which are provided with contact pads, and that said eye portions are interconnected through a nose portion which is also provided with contact pads.

8. A sleeping mask as defined in claim 1, characterized in that the length of said side parts is variable.

9. A sleeping mask as defined in claim 8, characterized in that a pair of transition portions are provided, each transition portion extending between said eye mask and one of said side parts, the transition portions being elastically stretchable.

10. A sleeping mask as defined in claim 9, characterized in that said transition portions have a minimum width adapted to an average distance between an upper line of an eyebrow and a lower edge of an eye of the user's head.

11. A sleeping mask as defined in claim 1, characterized in that a pair of transition portions are provided, each transition portion extending between said eye mask and one of said side parts, the transition portions being elastically stretchable.

12. A sleeping mask as defined in claim 11, characterized in that said transition portions have a minimum width adapted to an average distance between an upper line of an eyebrow and a lower edge of an eye of the users head.

13. A sleeping mask as defined in claim 5, characterized in that said eye mask comprises two eye portions which are provided with contact pads, and that said eye portions are interconnected through a nose portion which is also provided with contact pads.

* * * * *